(12) United States Patent
Kurachi et al.

(10) Patent No.: US 11,045,097 B2
(45) Date of Patent: Jun. 29, 2021

(54) BLOOD PRESSURE METER

(71) Applicant: SOCIONEXT INC., Yokohama (JP)

(72) Inventors: Ryusuke Kurachi, Yokohama (JP);
Masaya Tamamura, Yokohama (JP);
Masato Yoshioka, Yokohama (JP);
Hiroyuki Tomura, Yokohama (JP);
Amane Inoue, Yokohama (JP); Minoru Nakagawara, Sapporo (JP)

(73) Assignee: SOCIONEXT INC., Yokohama (JP)

( * ) Notice: Subject to any disclaimer, the term of this patent is extended or adjusted under 35 U.S.C. 154(b) by 432 days.

(21) Appl. No.: 16/138,586

(22) Filed: Sep. 21, 2018

(65) Prior Publication Data
US 2019/0014998 A1 Jan. 17, 2019

Related U.S. Application Data

(63) Continuation of application No. PCT/JP2016/062410, filed on Apr. 19, 2016.

(51) Int. Cl.
*A61B 5/022* (2006.01)
*A61B 5/0225* (2006.01)
(Continued)

(52) U.S. Cl.
CPC ...... *A61B 5/02233* (2013.01); *A61B 5/02007* (2013.01); *A61B 5/0225* (2013.01);
(Continued)

(58) Field of Classification Search
CPC ........... A61B 5/02; A61B 5/021; A61B 5/022; A61B 5/0235; A61B 5/02233; A61B 5/0225
See application file for complete search history.

(56) References Cited

U.S. PATENT DOCUMENTS

| 4,406,289 A | 9/1983 | Wesseling et al. |
| 4,510,940 A * | 4/1985 | Wesseling .......... A61B 5/02255 600/480 |

(Continued)

FOREIGN PATENT DOCUMENTS

| EP | 0926980 A2 | 7/1999 |
| JP | S61-041434 A | 2/1986 |

(Continued)

OTHER PUBLICATIONS

European Extended Search Report issued by the European Patent Office in corresponding European Application No. 16899386.3, dated Sep. 5, 2019.
(Continued)

*Primary Examiner* — Daniel L Cerioni
*Assistant Examiner* — Raymond P Dulman
(74) *Attorney, Agent, or Firm* — Arent Fox LLP

(57) ABSTRACT

The purpose of the present invention is to reduce the influence of pump ripple and to achieve fast control of cuff pressure with a general purpose magnetic valve when continuously measuring blood pressure. A blood pressure meter 1 includes a pump 11, a cuff 12 to be mounted on the site of blood pressure measurement of a subject, a first valve 13, a first pressure sensor 14, a detection sensor 18, a second valve 23, and a second pressure sensor 24. The blood pressure meter 1 also includes a valve opening adjustment unit 42 and a blood pressure measurement unit 43. The first valve 13 adjusts discharge volume of the pump 11 and the second valve 23 adjusts cuff pressure inside the cuff 12. The first pressure sensor 14 detects the discharge pressure of the pump 11, the second pressure sensor 24 detects the cuff pressure, and the detection sensor 18 detects the amount of light associated with the volume of the artery at the site of blood pressure measurement of the subject. The valve open-
(Continued)

ing adjustment unit 42 acquires the discharge pressure, the cuff pressure, and the amount of light, and adjusts the openings of the first valve 13 and the second valve 23. The blood pressure measurement unit 43 measures the blood pressure of the subject on the basis of the cuff pressure.

3 Claims, 11 Drawing Sheets

(51) Int. Cl.
*A61B 5/0235* (2006.01)
*A61B 5/024* (2006.01)
*A61B 5/1455* (2006.01)
*A61B 5/02* (2006.01)
*A61B 5/021* (2006.01)

(52) U.S. Cl.
CPC ........ *A61B 5/0235* (2013.01); *A61B 5/02241* (2013.01); *A61B 5/02422* (2013.01); *A61B 5/14551* (2013.01); *A61B 5/02141* (2013.01); *A61B 2562/04* (2013.01)

(56) References Cited

U.S. PATENT DOCUMENTS

| | | | | |
|---|---|---|---|---|
| 4,539,997 | A | * | 9/1985 | Wesseling .......... A61B 5/02255 600/480 |
| 6,319,205 | B1 | | 11/2001 | Goor et al. |
| 6,669,648 | B1 | | 12/2003 | Fortin et al. |
| 2007/0032729 | A1 | | 2/2007 | Fortin |
| 2011/0263992 | A1 | * | 10/2011 | Guelen .............. A61B 5/02255 600/493 |
| 2012/0245471 | A1 | * | 9/2012 | Langewouters ... A61B 5/02241 600/473 |
| 2014/0142434 | A1 | * | 5/2014 | Nitzan ................. A61B 5/0261 600/473 |
| 2015/0359437 | A1 | * | 12/2015 | Maltz .................. A61B 5/6824 600/481 |

FOREIGN PATENT DOCUMENTS

| | | | |
|---|---|---|---|
| JP | S61-119238 | A | 6/1986 |
| JP | S63-29616 | A | 2/1988 |
| JP | H05-049605 | A | 3/1993 |
| JP | H08-332173 | A | 12/1996 |
| JP | 2000-515789 | A | 11/2000 |
| JP | 2007-508872 | A | 4/2007 |
| JP | 2012-205719 | A | 10/2012 |
| JP | 2012210374 | A | 11/2012 |
| JP | 2015-188646 | A | 11/2015 |

OTHER PUBLICATIONS

European Office Action issued by the European Patent Trademark Office in corresponding European Patent Application No. 16899386.3, dated Jul. 31, 2020.

International Search Report of related International Patent Application No. PCT/JP2016/062410 dated Jul. 26, 2016.

Written Opinion of related International Patent Application No. PCT/JP2016/062410, with partial translation, dated Jul. 26, 2016.

* cited by examiner

BLOOD PRESSURE METER

CROSS-REFERENCE TO RELATED APPLICATION

This application is continuation application of the International Application PCT/JP2016/062410, filed on Apr. 19, 2016, and designated the U.S., the entire contents of which are incorporated herein by reference.

FIELD

The present invention elates to a blood pressure meter.

BACKGROUND

Various blood pressure meters are known. For example, it is known to measure the blood pressure of a subject in accordance with differential pressure between variable pressure within a pressure chamber of a finger probe and constant pressure between a pair of solenoid valves (for example, see Patent Literature 1). Further, it is known to reduce the time until cuff pressure is raised by starting measurement of blood pressure by discharging air into the cuff from a pressure vessel that causes the pressure vessel and the cuff to communicate with each other after raising pressure inside the pressure vessel by a pump i (for example, see Patent Literature 2). Further, it is known to detect torsion of an air supply hose connected to a cuff by connecting a first pressure sensor and a second pressure sensor to an air supply path to the cuff and by comparing a detected value of the first pressure sensor and a detected value of the second pressure sensor i (for example, see Patent Literature 3). Further, it is known to lower cuff pressure by opening an exit valve when the cuff pressure detected by a single pressure sensor is higher than predetermined threshold pressure and raising the cuff pressure by opening an entrance valve when the cuff pressure is lower than the predetermined threshold pressure (for example, see Patent Literatures 4 to 6). Further, it is known to adjust cuff pressure in each of a plurality of cuffs by detecting the cuff pressure inside each of the plurality of cuffs and controlling an electromagnetic valve in accordance with the detected cuff pressure is known (for example, see Patent Literature 7). Further, a volume compensation method is known as a method capable of continuous measurement for each heartbeat. High-speed control of cuff pressure to follow a change in pressure within an arterial blood vessel is necessary to implement the volume compensation method. Air is used for the cuff pressure control, since air is handled easily and high-speed control of cuff pressure is implemented by electrically controlling air pressure generated from a pressure source and a flow rate of an escape valve. Although an air pump of diaphragm type is generally used as the pressure source, ripple is included in the output of pressure and flow rate of the pump of diaphragm type, and therefore it is also necessary for high-speed control of the escape valve to follow a change in pressure of ripple, in addition to a change in arterial pressure. As above described, several techniques are known to perform high-speed pressure control for the volume compensation method it is known to perform high-speed control of an amount of escape of air pressure of a pressure source by using high-speed responsiveness of a piezoelectric element (the example, see Patent Literature 8). It is known that two electromagnetic valves are used, cuff pressure is measured by one pressure sensor, and an amount of pressure supplied is controlled by one of the electromagnetic valves and an amount of escape is controlled by the other electromagnetic valve so that the pressure becomes a control target value (for example, see Patent Literature 9).

CITATION LIST

Patent Literature

[Patent Literature 1] Japanese National Publication of International Patent Application No. 2000-515789
[Patent Literature 2] Japanese Laid Open Patent Publication No. 2015-188646
[Patent Literature 3] Japanese Laid Open Patent Publication No. 2012-205719
[Patent Literature 4] Japanese National Publication of international Patent Application No. 2007-508872
[Patent Literature 5] Japanese Laid Open Patent Publication No. 05-49605
[Patent Literature 6] Japanese Laid Open Patent Publication No. 63-29616
[Patent Literature 7] Japanese Laid Open Patent Publication No. 08-332173
[Patent Literature 8] U.S. Pat. No. 4,406,289
[Patent Literature 9] U.S. Pat. No. 6,669,648

SUMMARY

In one aspect, the blood pressure meter has a pump, a cuff attached to a blood pressure measurement region of a subject, a first valve, a second valve, a first pressure sensor, a second pressure sensor, an arterial volume information detection sensor, a valve opening adjuster, and a blood pressure measurement unit. The first valve is arranged between the pump and the cuff and adjusts the amount of discharge of the pump by adjusting the opening, and the second valve adjusts the cuff pressure inside the cuff by adjusting the opening. The first pressure sensor detects the discharge pressure of the pump, the second pressure sensor detects the cuff pressure, and the arterial volume information detection sensor detects arterial volume information relating to the arterial volume at the blood pressure measurement region of a subject. The valve opening adjuster acquires the discharge pressure, the cuff pressure, and the arterial volume information, and adjusts the first valve so that the discharge pressure becomes a control target value and adjusts the opening of the second valve so that the cuff pressure becomes a control target value. The blood pressure measurement unit measures the blood pressure of a subject based on the cuff pressure.

The object and advantages of the embodiments will be realized and attained by means of the elements and combination particularly pointed out in the claims.

It is to be understood that both the foregoing general description and the following detailed description are exemplary and explanatory and are not restrictive of the invention.

DESCRIPTION OF EMBODIMENTS

In the following, with reference to the drawings, a blood pressure meter according to an embodiment is explained. However, it should be understood that the present invention is not limited to the drawings or the embodiments described in the following.

(Configuration and Function of Related Blood Pressure Meter)

Figure 1:
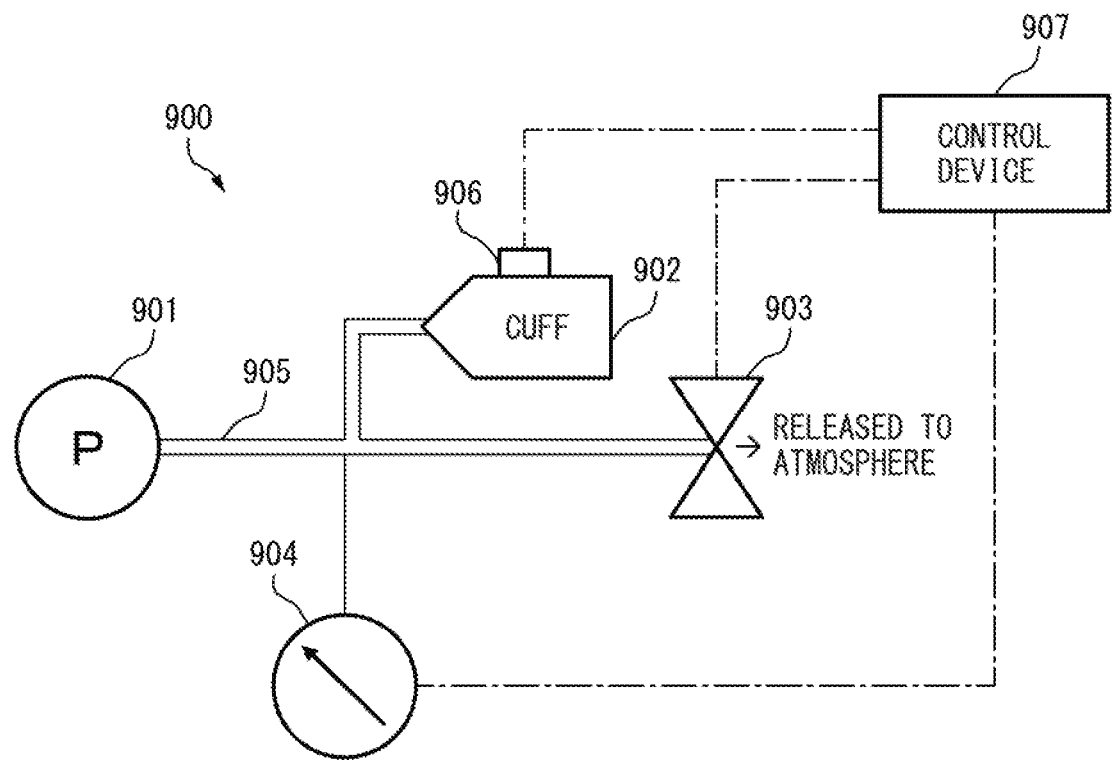
FIG. 1 is an outline configuration diagram of a related blood pressure meter.

FIG. 1 is an outline configuration diagram of a related blood pressure meter. In FIG. 1, the path of a signal is indicated by a one-dot chain line.

A blood pressure meter 900 has a pump 901, a cuff 902, an electromagnetic valve 903, a pressure sensor 904, a connection member 905, a light amount detection sensor 906, and a control device 907. The pump 901 takes in air in the atmosphere and pressurizes the air and discharges the pressurized air into the cuff 902 via the connection member 905. The cuff 902 includes a fluid bag that wraps and holds the blood pressure measurement region, such as a finger, and which expands when the air that is a pressure medium is injected from the pump 901 and contracts when the air is exhausted. The electromagnetic valve 903 is connected to the cuff 902 via the connection member 905 and enters the open state when an open instruction signal is input from the control device 907 and enters the closed state when a close instruction signal is input from the control device 907. The pressure sensor 904 is connected to the cuff 902 via the connection member 905, and detects cuff pressure, which is the internal pressure of the cuff, and outputs a cuff pressure signal indicating the cuff pressure to the control device 907. The connection member 905 is a tubular member formed by a flexible material, such as a synthetic resin, and exhausts air from the pump 901 and the cuff 902 to the electromagnetic valve 903 when the electromagnetic valve 903 enters the open state as well as injecting air from the pump 901 into the cuff 902. The light amount detection sensor 906 is a photoelectric sensor having a light-emitting element and a light-receiving element, not shown schematically, and detects the amount of light when the artery at the blood pressure measurement region to which the cuff 902 is attached is irradiated with light, that is, the arterial volume. A light amount signal indicating the detected arterial volume is output to the control device 907. The control device 907 has a storage unit, a processing unit, and an interface circuit and measures the blood pressure of a subject by the volume compensation method. The volume compensation method is a method in which the arterial volume is kept constant (volume compensation) by making the same value (by bringing into equilibrium) the external pressure applied from the outside by the cuff 902 and the blood vessel internal pressure of a person, which changes at all times, and the cuff pressure at this time is measured as the blood pressure value. Thus, it is necessary to change the cuff pressure by following the change in arterial volume accompanying the change in blood pressure. Further, for the determination of that the external pressure and the internal pressure become constant, the volume vibration method is used. The control device 907 measures the blood pressure of a subject from the cuff pressure as well as adjusting the cuff pressure so that the arterial volume at the blood pressure measurement region to which the cuff 902 is attached becomes constant based on the amount of light corresponding to the arterial volume by opening and closing the electromagnetic valve 903.

When measuring the blood pressure of a subject by the volume compensation method, the control device 907 varies the discharge pressure of the pump 901 between about 50 mmHg and 250 mmHg. In order for the discharge pressure to follow the change in arterial pressure, about 20 [Hz] is necessary for the varying frequency. Further, it is also necessary to suppress the ripple pressure variation generated from the pump 901.

Figure 2:
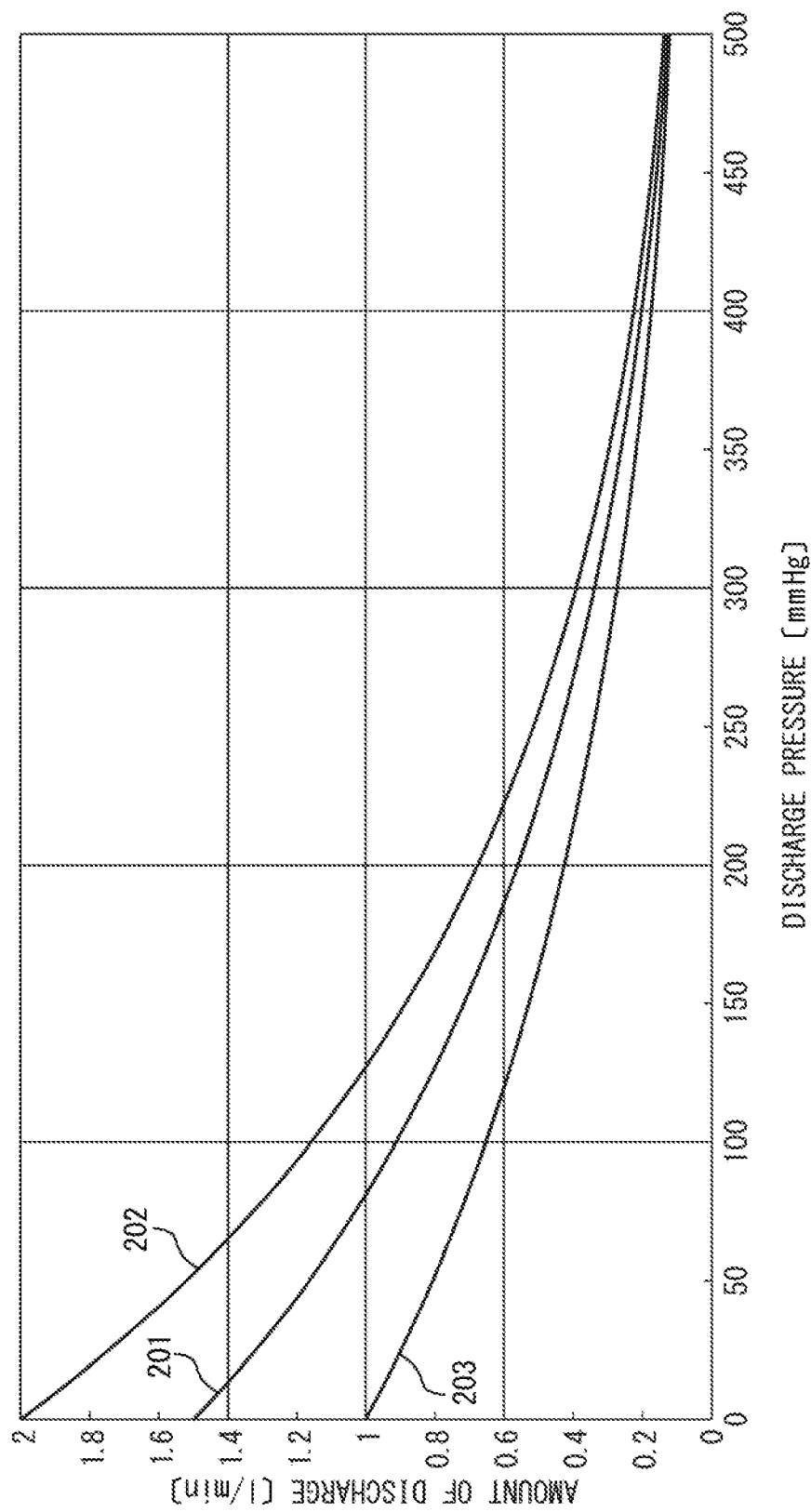
FIG. 2 is a diagram showing pressure discharge amount characteristics of the pump illustrated in FIG. 1.

FIG. 2 is a diagram showing pressure/discharge amount characteristics of the pump 901. In FIG. 2, the horizontal axis represents the discharge pressure [mmHg] and the vertical axis represents the amount of discharge [1 (liter)/min]. Further, a curved line 201 is a pressure/discharge amount curved line indicated generally and obtained by averaging the ripple components included in a diaphragm pump. A curved line 202 indicates pressure/discharge amount characteristics at the time of the maximum flow rate when the pump exhausts air. A curved line 203 indicates pressure/discharge amount characteristics at the time of the minimum flow rate when the pump takes in air.

Figure 3:
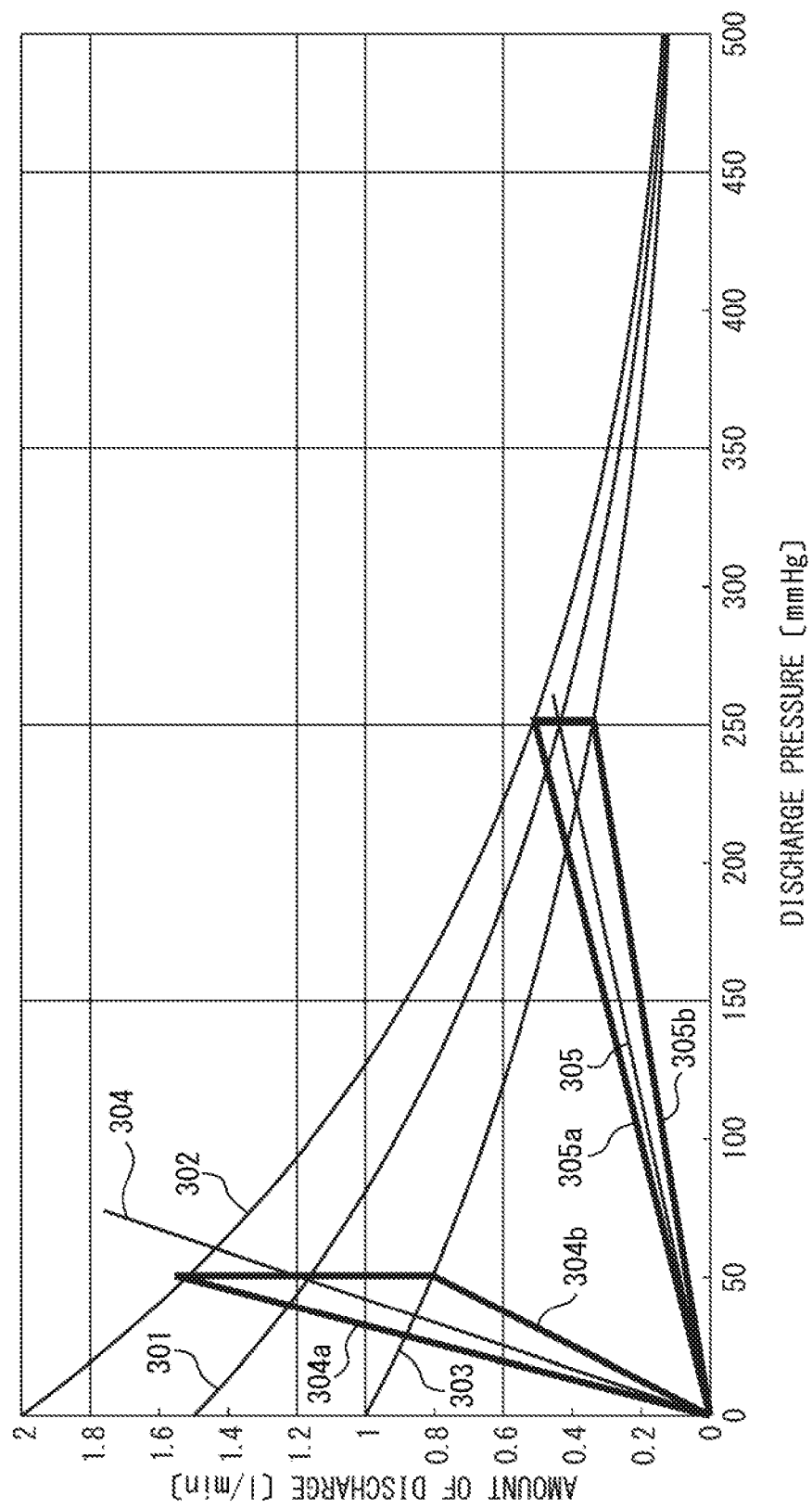
FIG. 3 is a diagram for explaining problems of the blood pressure meter illustrated in FIG. 1.

FIG. 3 is a diagrams for explaining problems of the blood pressure meter 900. In FIG. 3, the horizontal axis represents the discharge pressure [mmHg] and the vertical axis represents the amount of discharge [1/min]. Further, a curved line 301 indicates pressure/discharge amount characteristics obtained by averaging the ripple components included in the pump, like the curved line 201. A curved line 302 indicates pressure/discharge amount characteristics at the time of the maximum flow rate when the pump exhausts air, like the curved line 202. A curved line 303 indicates pressure/discharge amount characteristics at the time of the minimum flow rate when the pump takes in air, like the curved line 203. A straight line 304 indicates a load straight line corresponding to the curved line 301 of the electromagnetic valve 903 when the discharge pressure of the pump 901 is 50 [mmHg] and a straight line 305 indicates a load straight line corresponding to the curved line 301 of the electromagnetic valve 903 when the discharge pressure of the pump 901 is 250 [mmHg].

When the electromagnetic valve 903 is controlled so gas to enter the state of the load straight line 304 so that the discharge pressure of the pump 901 becomes 50 [mmHg], if the pump moves to the pressure/discharge amount characteristics 302 when the pump exhausts air, the discharge pressure becomes 50 [mmHg] or higher as indicated by an intersection of the curved line 302 and the straight line 304. On the other hand, if the pump moves to the pressure/discharge amount characteristics 302 when the pump takes in air, the discharge pressure becomes 50 [mmHg] or lower as indicated by an intersection of the curved line 303 and the straight line 304. In order to keep the discharge pressure constant at 50 [mmHg] without being affected by the ripple variation of the pump, it is necessary to change the slope angle of the load straight line 304 between 304a and 304b by controlling the amount of discharge of the electromagnetic valve 903. On the other hand, the ripple frequency of the pump is determined by the rotation speed and the structure of the motor and the ripple frequency may becomes 100 Hz or higher. Thus, it is necessary for the electromagnetic valve 903 to implement the change in slope between the load straight lines 304a and 304b at a frequency of 100 [Hz] or higher. Further, the larger the angle formed by the load straight lines 304a and 304b, the more the high-speed performance is required for the electromagnetic valve 903. The load straight line that the electromagnetic valve 903 should control when the discharge pressure of the pump 901 is 250 [mmHg] is 305 and it is shown that in order to remove the influence of the ripple component, it is necessary to change the load straight line in the range between 305a and 305b. Further, the angle formed by 305a and 305b) is smaller than that of 5 [mmHg]. Thus, the higher the pressure, the more the high-speed performance required for the electromagnetic valve 903 is relaxed.

(Outline of Blood Pressure Meter According to Embodiment)

High-speed control of cuff pressure including ripple of a diaphragm pump is implemented by using an inexpensive, general-purpose electromagnetic valve in a blood pressure meter of the volume compensation method according to an embodiment. The blood pressure meter according to the embodiment has a first valve that adjusts the amount of discharge of air that is injected into the inside of a cuff from a pump, a second valve that adjusts the cuff pressure inside the cuff, a first pressure sensor that detects the discharge pressure of the pump, and a second pressure sensor that detects the cuff pressure. The blood pressure meter according to the embodiment may reduce the variation in the discharge amount characteristics of the pump and to prevent the cuff pressure from deviating from desired pressure by adjusting the amount of discharge of the pump by the first valve.

Figure 4:
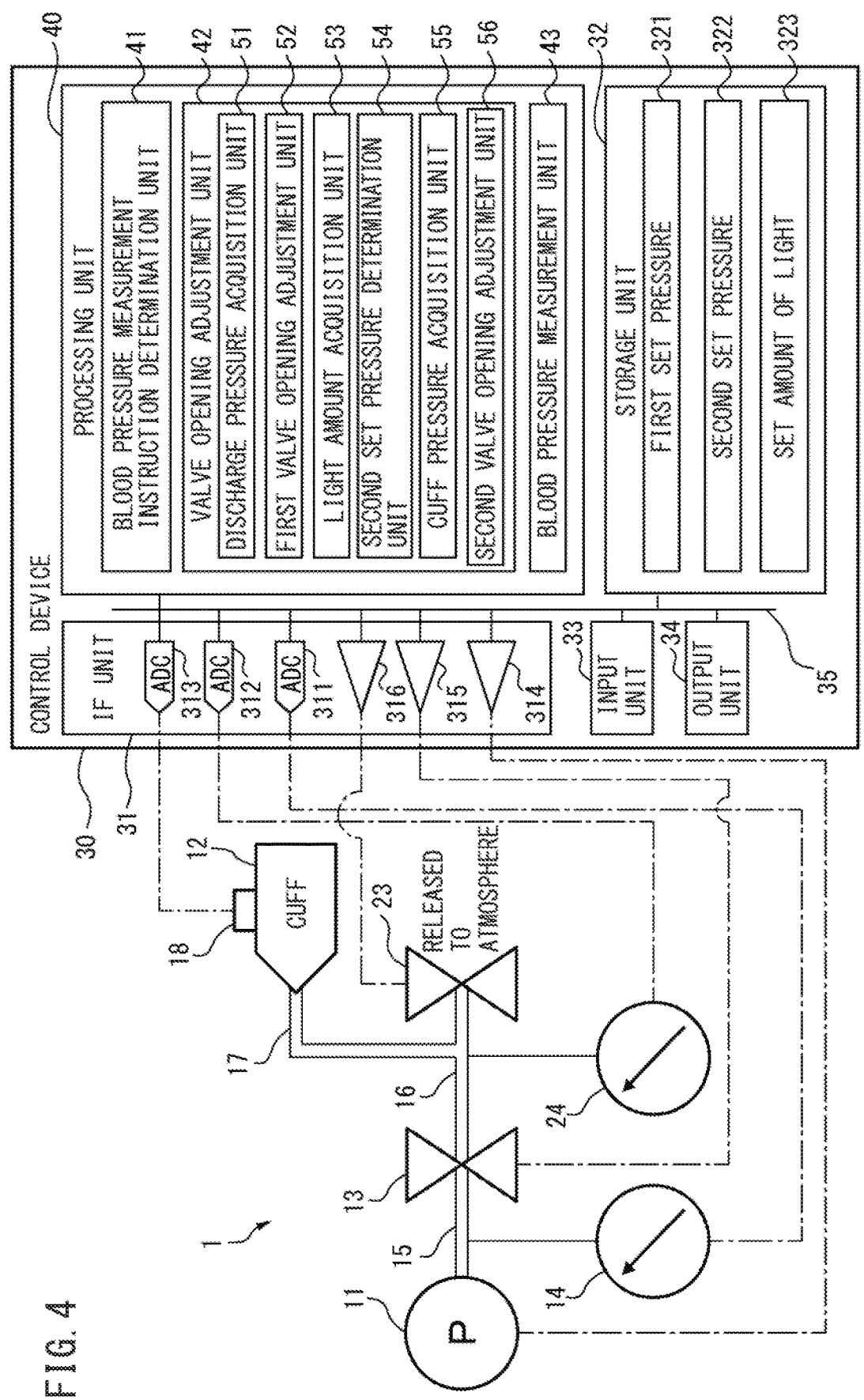
FIG. 4 is an outline configuration diagram of the blood pressure meter according to the embodiment

FIG. 4 is an outline configuration diagram of the blood pressure meter according to the embodiment. In FIG. 4, the path of a signal is indicated by a one-dot chain line.

A blood pressure meter 1 has a pump 11, a cuff 12, a first valve 13, a first pressure sensor 14, a pump connection member 15, a first cuff connection member 16, a second cuff connection member 17, a light amount detection sensor 18, a second valve 23, a second pressure sensor 24, and a control device 30. The pump 11 is a diaphragm pump in one example and takes in air in the atmosphere and pressurizes the air and discharges the pressurized air to the cuff 12 via the first valve 13. The pump 11 starts when receiving a start instruction signal indicating instructions to start the pump 11 and stops when receiving a pump stop instruction signal indicating instructions to stop the pump 11.

Figure 5:
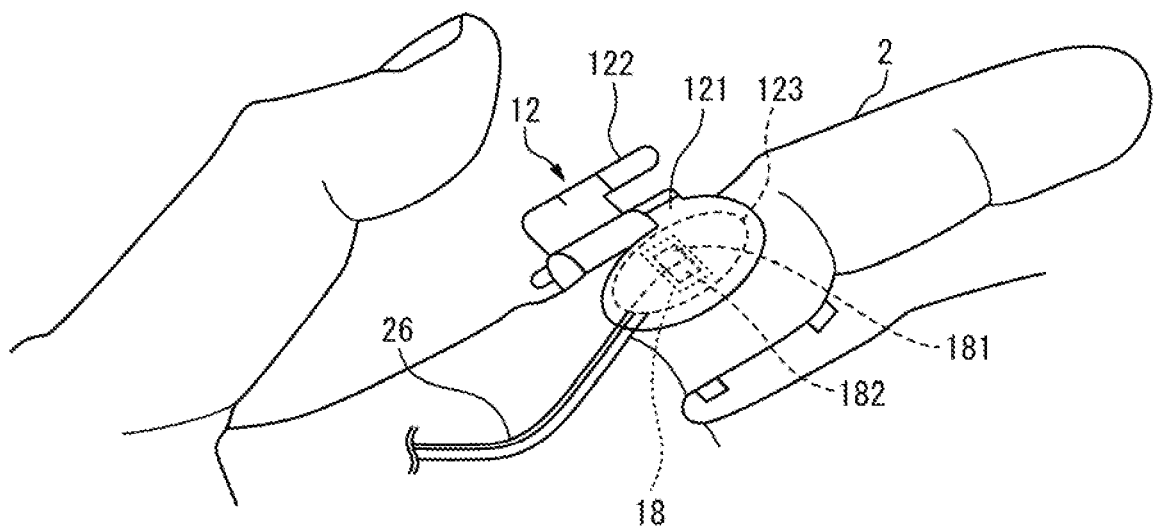
FIG. 5 is a diagram showing a state where the cuff illustrated in FIG. 4 is attached to the finger of a subject.

FIG. 5 is a diagram showing a state where the cuff 12 is attached to the finger of a subject.

The cuff 12 has a belt unit 121, a cuff fixing unit 122, and a shrinkage fluid bag 123 that is included in the belt unit and wraps and holds a forefinger 2 of a subject, which is the blood pressure measurement region. The belt unit 121 further includes the light amount detection sensor 18 having a light-emitting element 181 and a light-receiving element 182. The cuff fixing unit 122 is a member capable of rotating between an open position and a fixed position and when the cuff fixing unit 122 is located at the open position, the forefinger 2 of the subject may be inserted and when the cuff fixing unit 122 is located at the fixed position, the forefinger 2 of the subject is wrapped and held. The shrinkage fluid bag 123 expands when air, which is a pressure medium, is injected from the pump 11 via a second cuff connection member 26, which is a tubular member formed by a flexible material, such as a synthetic resin. On the other hand, the shrinkage fluid bag 123 contracts when air is exhausted.

Figure 6:
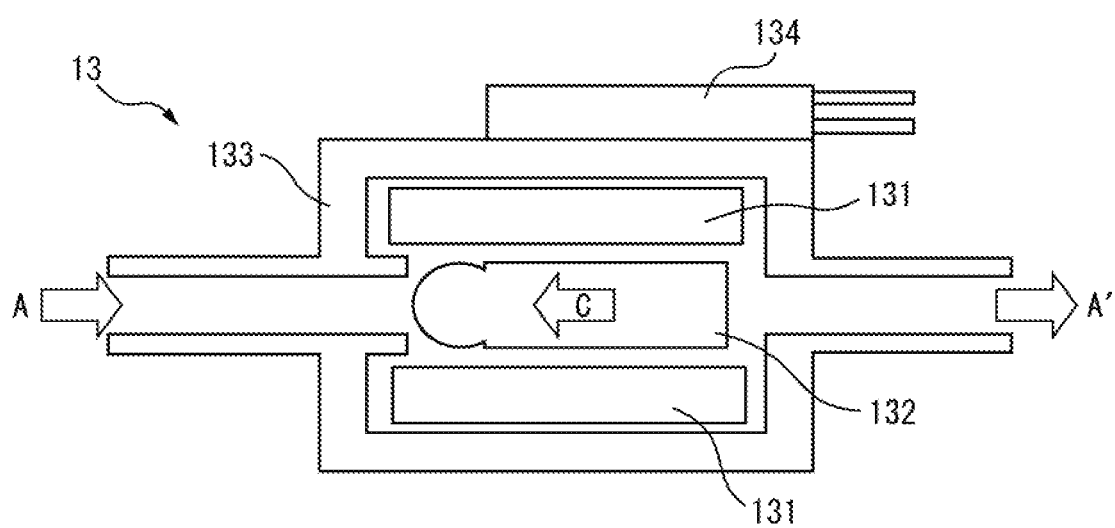
FIG. 6 is an outline configuration diagram of the first valve illustrated in FIG. 4.

FIG. 6 is an outline configuration diagram of the first valve 13. In FIG. 6, arrows A and A' indicate a flow of air and an arrow C indicates the direction in which an actuator 132 of the first valve 13 moves when an electric current is supplied to an electromagnetic coil.

The first valve 13 is an electromagnetic valve having an electromagnetic coil 131, the actuator 132, a valve seat 133, and an electric current acquisition unit 134. The electromagnetic coil 131 generates a magnetic field in accordance with an electric current that is input from a power source device, not shown schematically, via the electric current acquisition unit 134. The generated magnetic field acts so that a magnetic circuit formed by the valve seat 133 and the actuator 132 closes and the actuator 132 moves in the close direction indicated by the arrow C. When the actuator 132 moves in the close direction and comes into perfect contact with the valve seat 133, the first valve enters the closed state. Further, when the electromagnetic supply to the electromagnetic coil 131 is shut off, the actuator 132 moves in the open direction opposite to the close direction indicated by the arrow C by the force of the flow of air indicated by the arrow A.

When the blood pressure meter 1 operates, the opening of the first valve 13 is adjusted by the control device 30 so that the pressure of the first pressure sensor 14 becomes set pressure. The first valve 13 functions as a throttle valve that performs adjustment so that the amount of discharge of air discharged to the cuff 12 from the pump 11 is constant at all times irrespective of the variation in the load.

The configuration of the second valve 23 is the same as the configuration of the first valve 13, or as the second valve 23, a valve whose structure is simpler than that of the first valve 13 may be used, and therefore detailed explanation of the configuration of the second valve 23 is omitted here. The opening of the second valve 23 is adjusted by the control device 30 so that the pressure of the second pressure sensor 24 becomes set pressure. Thus, the second valve 23 functions as a valve that adjusts the cuff pressure by exhausting the air of a constant flow rate supplied from the first valve and the air from the cuff 12.

The first pressure sensor 14 is, in one example, a strain gauge type pressure sensor including a piezoresistive element. The first pressure sensor 14 detects the pressure inside the pump connection member 15 arranged between the pump 11 and the first valve. The pressure inside the pump connection member 15 is the discharge pressure of the pump 11. The discharge pressure of the pump 11 is determined by the discharge flow rate of the pump 11 and the flow rate resistance of the first valve 13. The first pressure sensor 14 outputs a discharge pressure signal indicating the detected discharge pressure to the control device 30.

The second pressure sensor 24 is, in one example, a strain gauge type pressure sensor including a piezoresistive element like the first pressure sensor 14. The second pressure sensor 24 detects the cuff pressure inside the cuff 12 via the first cuff connection member 16 and the second cuff connection member 17. The cuff pressure is determined by the air of a constant flow rate supplied from the first valve 13 and the flow rate resistance of the valve of the second valve 23. The second pressure sensor 24 outputs a cuff pressure signal indicating the detected cuff pressure to the control device 30.

Figure 7A:
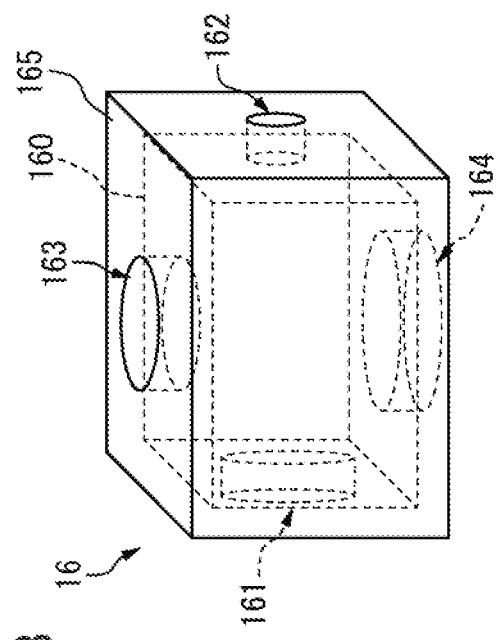
FIG. 7A is a perspective diagram of the pump connection member illustrated in FIG. 4.
Figure 7B:
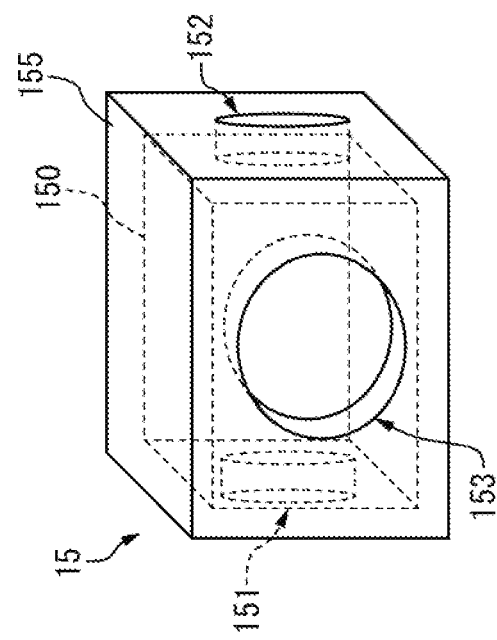
FIG. 7B is a perspective diagram of the first cuff connection member illustrated in FIG. 4.
Figure 7C:
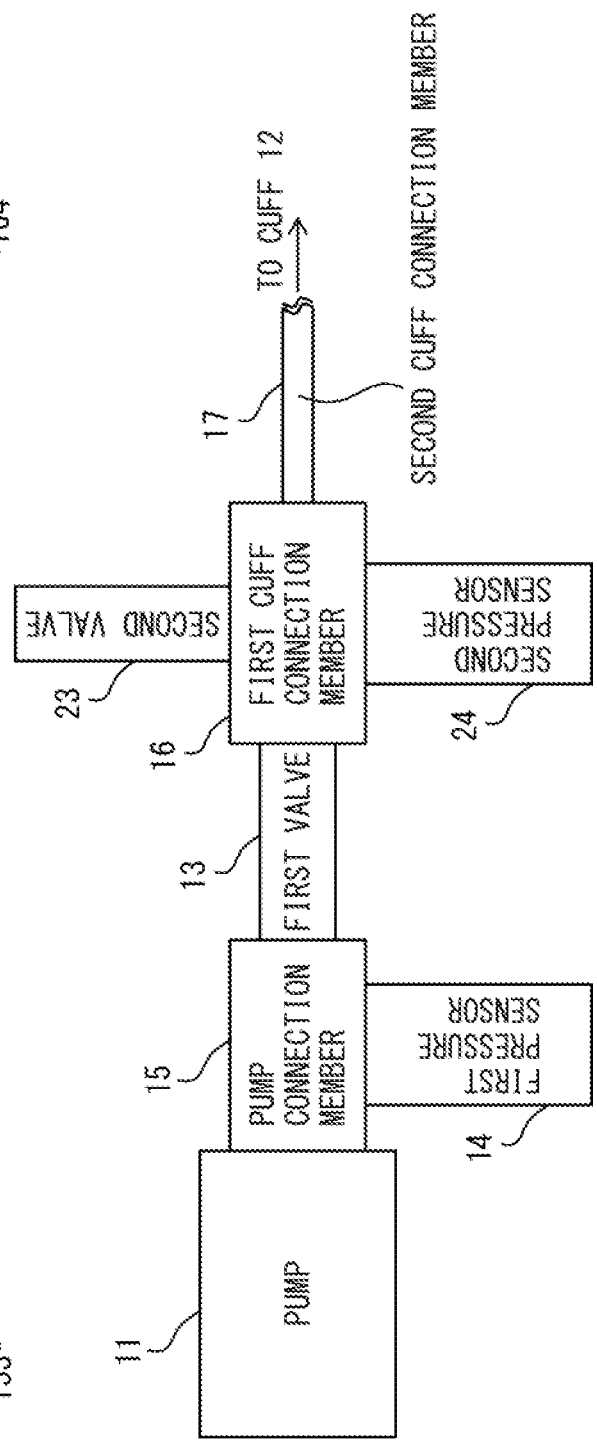
FIG. 7C is a partial front diagram of the blood pressure meter illustrated in FIG. 4.

FIG. 7A is a perspective diagram of the pump connection member 15, FIG. 7B is a perspective diagram of the first cuff connection member 16, and FIG. 7C is a partial front diagram of the blood pressure meter 1.

Inside the pump connection member 15, a pressure chamber 150 is formed and at the same time, a first through-hole 151, a second through-hole 152, and a third through-hole 153 are formed, each penetrating from an external wall 155 up to the pressure chamber 150. The pump 11 is inserted into the first through-hole 151, the first valve 13 is inserted into the second through-hole 152, and the first pressure sensor 14 is inserted into the third through-hole 153.

Inside the first cuff connection member 16, a pressure chamber 160 is formed and at the same time, a first through-hole 16, a second through-hole 162, a third through-hole 163, and a fourth through-hole 164 are formed, each penetrating from an external wall 165 up to the pressure chamber 160. The first valve 13 is inserted into the first through-hole 161, into the second through-hole 162, the second cuff connection member 17 is inserted Into the first through-hole 161, the second valve 23 is inserted into the third through-hole 163, and the second sensor 24 is inserted into the fourth through-hole 164.

The second cuff connection member 17 is a tubular member formed by a flexible material, such as a synthetic resin, and one end thereof is connected to the cuff 12 and the other end is inserted into the second through-hole of the first cuff connection member 16.

The total volume of the inside of the cuff 12, the pressure chamber 160 of the first cuff connection member 16, and the inside of the second cuff connection member 17 is smaller than or equal to 20 [ml].

The light amount detection sensor 18 is a photoelectric sensor having the light-emitting element 181 and the light-receiving element 182 and detects the amount of light when the artery at the blood pressure measurement region to which the cuff 902 is attached is irradiated with light. The light-receiving element 182 of the light amount detection sensor 18 receives an amount of light in accordance with the amount of hemoglobin flowing through the artery from the light-emitting element 181 and outputs a light amount signal indicating the received amount of light to the control device 30. The amount of light detected by the light amount detection sensor 18 is arterial volume information relating to the arterial volume in the forefinger 2 of a subject, which is the blood pressure measurement region. The light amount detection sensor 18 is an arterial volume information detection sensor that detects arterial volume information relating to the arterial volume in the forefinger 2 of a subject.

The control device 30 has an interface unit 31, a storage unit 32, an input unit 33, an output unit 34, a bus 35, and a processing unit 40. The bus 35 connects the storage unit 32, the input unit 33, the output unit 34, and the processing unit 40 to one another so as to be capable of communication.

The interface unit 31 has a first AD converter 311, a second AD converter 312, a third AD converter 313, a first transmission circuit 314, a second transmission circuit 315, and a third transmission circuit 316.

The first AD converter 311 converts a discharge pressure signal that is input from the first pressure sensor 14 from an analog signal into a digital signal and outputs the digital signal to the processing unit 40 via the bus 35. The second AD converter 312 converts a cuff pressure signal that is input from the second pressure sensor 24 from an analog signal into a digital signal and outputs the digital signal to the processing unit 40 via the bus 35. The third AD converter 313 converts a light amount signal that is input from the light amount detection sensor 18 from an analog signal into a digital signal and outputs the digital signal to the processing unit 40 via the bus 35.

The first transmission circuit 314 amplifies the start instruction signal and the pump stop instruction signal and transmits them to the pump 11. The second transmission circuit 315 transmits a first valve close instruction signal and a first valve open instruction signal to the first valve 13. The first valve close instruction signal is a signal indicating that the opening of the first valve 13 is reduced by a change opening and the first valve open instruction signal is a signal indicating that the opening of the first valve 13 is increased by a predetermined change opening. The third transmission circuit 316 transmits a second valve close instruction signal and a second valve open instruction signal to the second valve 23. The second valve close instruction signal indicates that the opening of the second valve 23 is reduced and the second valve open instruction signal indicates that the opening of the second valve 23 is increased.

The storage unit 32 has, for example, a semiconductor memory and stores driver programs, an operating system, application programs, and data used for arithmetic operation processing by the processing unit 40. The storage unit 32 stores first set pressure 321, second set pressure 322, and a set amount of light 323. The set amount of light 323 is determined from the difference between the amount of light detected by the light amount detection sensor 18 and the volume compensation value determined by the volume vibration method, and the first set pressure 321 is a target value in order to achieve the set amount of light 323. The first set pressure 321 is, in one example, 450 [mmHg]. The second set pressure 323 is a target value of the cuff pressure when the processing unit 40 measures the blood pressure of a subject and is changed in accordance with the amount of light detected by the light amount detection sensor 18.

Further, the storage unit 32 stores blood pressure measurement programs for measuring the blood pressure of a subject as application programs. Computer programs may be installed in the storage unit 32 from a computer-readable portable storage medium, for example, such as a CD-ROM and a DVD-ROM, by using a publicly known setup program.

The input unit 33 may be any device which may input data and for example, is a touch panel, and a keyboard. A subject may input a character, a figure, and a symbol by using the input unit 33. When the input unit 33 generates is operated by a subject, the input unit 33 generates a signal corresponding to the operation. Then, the generated signal is supplied to the processing unit 40 as instructions of the subject.

The output unit 34 may be any device which may display a video, and an image and for example, is a liquid crystal display, an organic EL (Electro-Luminescence) display, or the like.

The output unit 34 displays a video in accordance with video data supplied from the processing unit 40, and an image in accordance with image data.

The processing unit 40 has one or a plurality of processors and peripheral circuits thereof. The processing unit 40 performs various kinds of arithmetic operation processing and is, for example, a CPU (Central Processing Unit). The processing unit 40 controls the interface unit 31 so that the various kinds of arithmetic operation processing are performed by an appropriate procedure in accordance with programs stored in the storage unit 32. The processing unit 40 performs processing based on programs (driver program, operating system program, application program) stored in the storage unit 32. Further, the processing unit 40 may execute a plurality of programs (application programs) in parallel.

The processing unit 40 has a blood pressure measurement instruction determination unit 41, a valve opening adjustment unit 42, and a blood pressure measurement unit 43. The valve opening adjustment unit 42 has a discharge pressure acquisition unit 51, a first valve opening adjustment unit 52, a light amount acquisition unit 53, a second set pressure determination unit 54, a cuff pressure acquisition unit 55, and a second valve opening adjustment unit 56. Each unit included in the processing unit 40 is a function module that is implemented by a program executed on a processor included in the processing unit 40. Alternatively, each unit included in the processing unit 40 may be mounted on the blood pressure meter 1 as an independent integrated circuit, a microprocessor, or firmware.

(Blood Pressure Measurement Processing by Blood Pressure Meter According to Embodiment)

Figure 8:
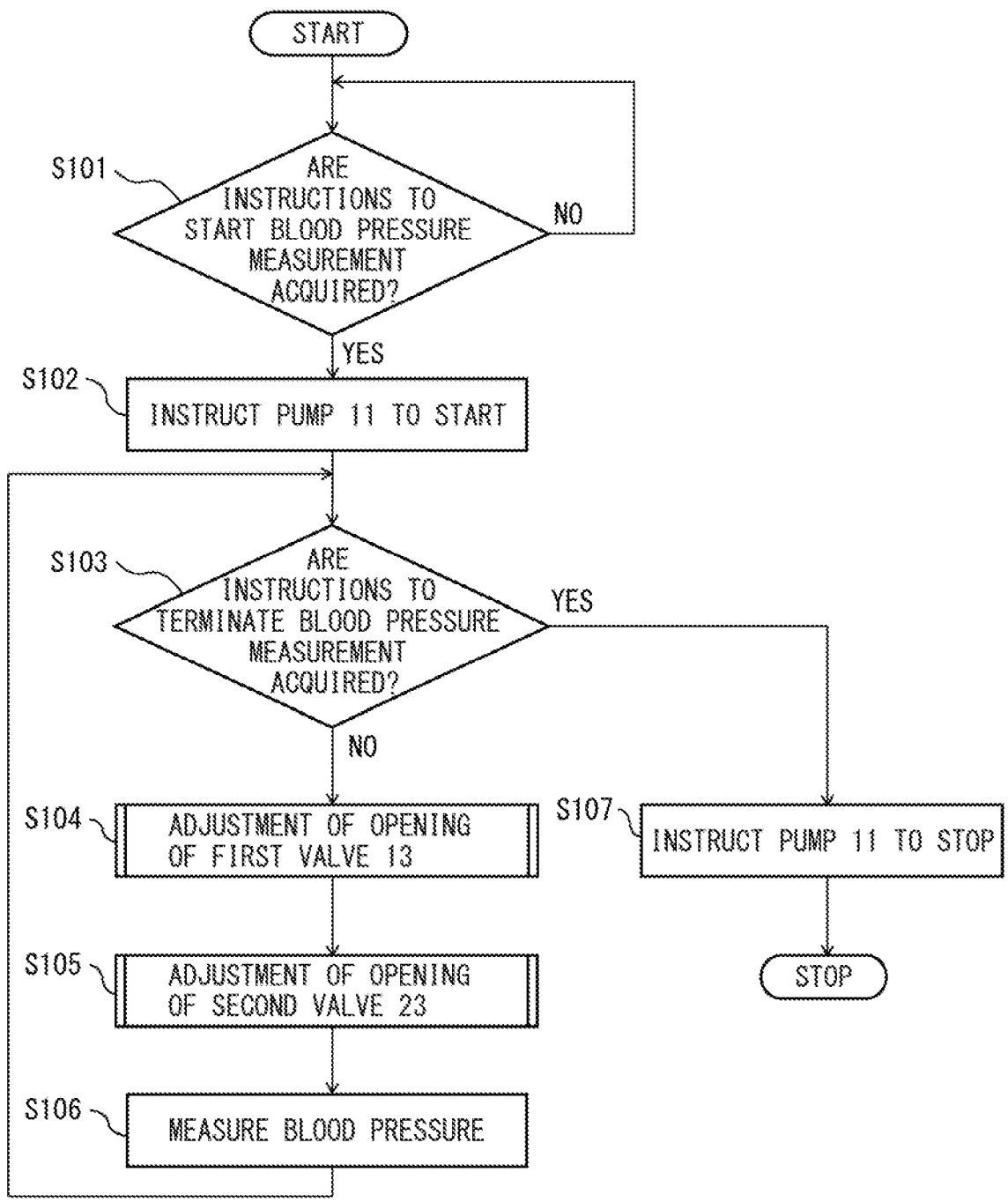
FIG. 8 is a flowchart of blood pressure measurement processing by the blood pressure meter illustrated in FIG. 4.

FIG. 8 is a flowchart of blood pressure measurement processing by the blood pressure meter 1. The blood pressure measurement processing shown in FIG. 8 is performed mainly by the processing unit 40 in cooperation with each element of the blood pressure meter 1 based on a program stored in advance in the storage unit 32.

First, the blood pressure measurement instruction determination unit 41 determines whether instructions to start blood pressure measurement are acquired from a subject via the input unit 33 (S101). The blood pressure measurement instruction determination unit 41 repeats the processing at S101 until determining that instructions to start blood pressure measurement are acquired (S101—YES). When the blood pressure measurement instruction determination unit 41 determines that instructions to start blood pressure measurement are acquired (S101—YES), the blood pressure measurement instruction determination unit 41 instructs the pump 11 to start by transmitting a start instruction signal indicating instructions to start the pump 11 to the pump 11 via the first transmission circuit 314 (S102). When the pump 11 receives the start instruction signal, the pump 11 starts.

Next, the blood pressure measurement instruction determination unit 41 determines whether instructions to terminate blood pressure measurement are acquired from a subject via the input unit 33 (S103). When it is determined that instructions to terminate blood pressure measurement are not acquired (S103—NO), the valve opening adjustment unit 42 adjusts the openings of the first valve 13 and the second valve 23. First, the valve opening adjustment unit 42 acquires the discharge pressure of the pump 11 and adjusts the opening of the first valve 13 so that the acquired discharge pressure coincides with the first set pressure (S104).

Next, the valve opening adjustment unit 42 adjusts the opening of the second valve 23 so that the arterial volume obtained by the light amount acquisition unit 53 coincides with the volume compensation value (S105).

Next, the blood pressure measurement unit 43 estimates the cuff pressure when the opening of the second valve 23 is adjusted at S105 as the blood pressure of a subject (S106) and outputs the measured blood pressure via the output unit 34.

Next, the processing returns to S103 and by the processing at S103 to S106 being repeated until the blood pressure measurement instruction determination unit 41 determines that instructions to terminate blood pressure measurement are acquired (S103—YES), the blood pressure of a subject is measured continuously by the blood pressure meter 1.

Then, the blood pressure measurement instruction determination unit 41 determines that instructions to terminate blood pressure measurement are acquired (S103—YES), the blood pressure measurement instruction determination unit 41 instructs the pump 11 to stop by transmitting a stop instruction signal indicating instructions to stop the pump 11 to the pump 11 via the first transmission circuit 314 (S102). When the pump II receives the stop instruction signal, the pump 11 stops.

Figure 9:
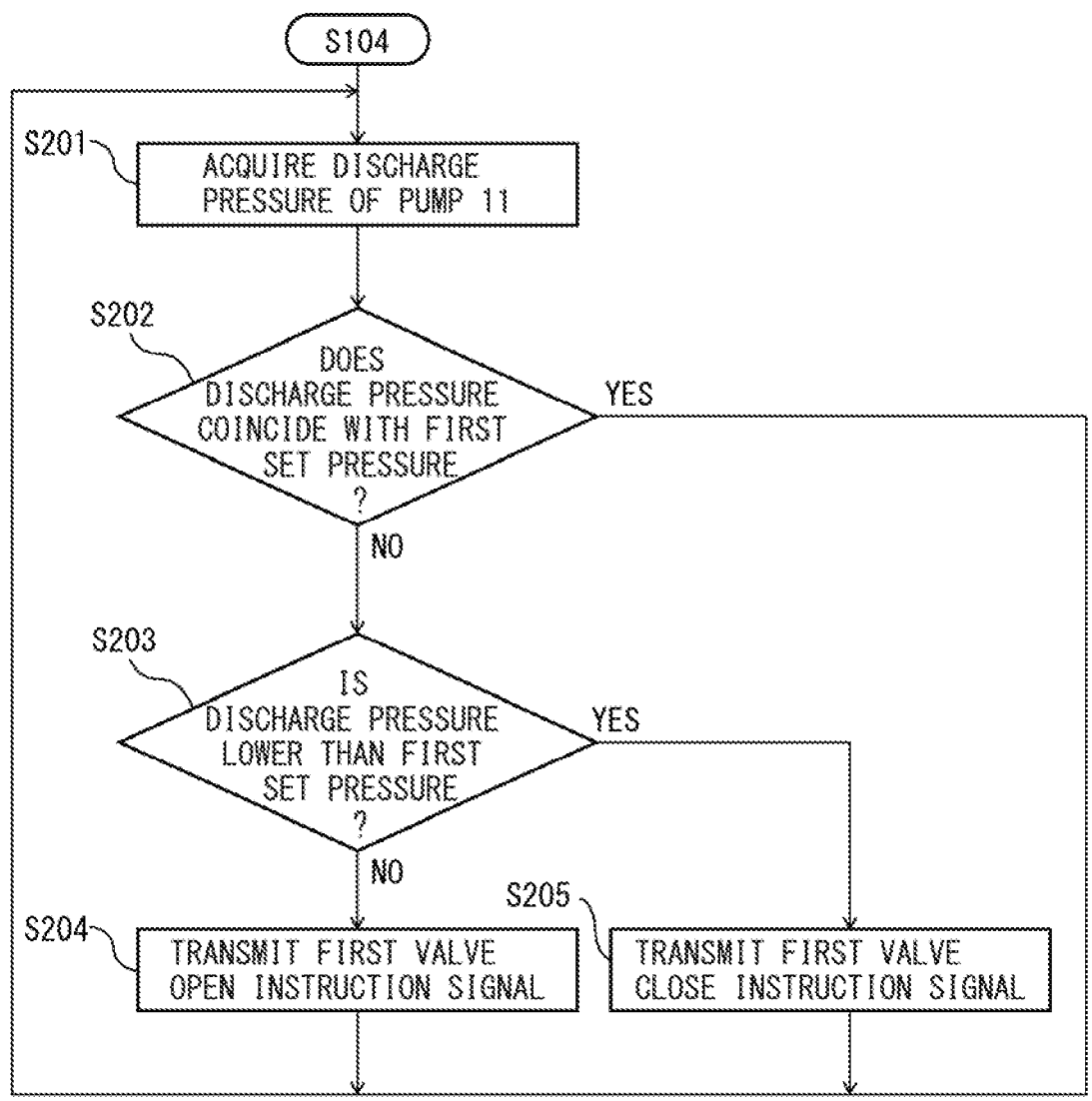
FIG. 9 is a flowchart showing more detailed processing of the processing shown at S104 illustrated in FIG. 8.

FIG. 9 is a flowchart showing more detailed processing of the processing shown at S104.

First, the discharge pressure acquisition unit 51 acquires the discharge pressure of the pump 11 corresponding to the discharge pressure signal transmitted from the first pressure sensor 14 via the first AD converter 311 (S201).

Next, the first valve opening adjustment unit 52 determines whether the acquired discharge pressure coincides with the first set pressure 321 stored in the storage unit 32 (S202). When the first valve opening adjustment unit 52 determines that the acquired discharge pressure does not coincide with the first set pressure 321 stored in the storage unit 32 (S202—NO), the first valve opening adjustment unit 52 determines whether the acquired discharge pressure is lower than the first set pressure 321 stored in the storage unit 32 (S203).

When the first valve opening adjustment unit 52 determining that the acquired discharge pressure is lower than the first set pressure 321 stored in the storage unit 32 (S203—YES), the first valve opening adjustment unit 52 transmits the first valve open instruction signal to the first valve 13 via the second transmission circuit 315 (S204). When the first valve 13 receives the first valve open instruction signal, the first valve 13 increases the opening by a predetermined change opening and the processing returns to S201.

On the other hand, when the first valve opening adjustment unit 52 determines that the acquired discharge pressure is higher than the first set pressure 321 stored in the storage unit 32 (S203—NO), the first valve opening adjustment unit 52 transmits the first valve close instruction signal to the first valve 13 via the second transmission circuit 315 (S205). When the first valve 13 receives the first valve close instruction signal, the first valve 13 reduces the opening by a predetermined change opening and the processing returns to S201.

The processing at S201 to S205 is repeated until it is determined that the acquired discharge pressure coincides with the first set pressure 321 stored in the storage unit 32 (S202—YES). By the processing at S201 to S205 being repeated, the first valve opening adjustment unit 52 adjusts the opening of the first valve 13 so that the discharge pressure of the pump 11 coincides with the first set pressure stored in the storage unit 32. When the first valve opening adjustment unit 52 determines that the discharge pressure of the pump 11 coincides with the first set pressure 321 stored in the storage unit 32 (S202—YES), the processing returns to S201 with the first valve opening being maintained.

Figure 10:
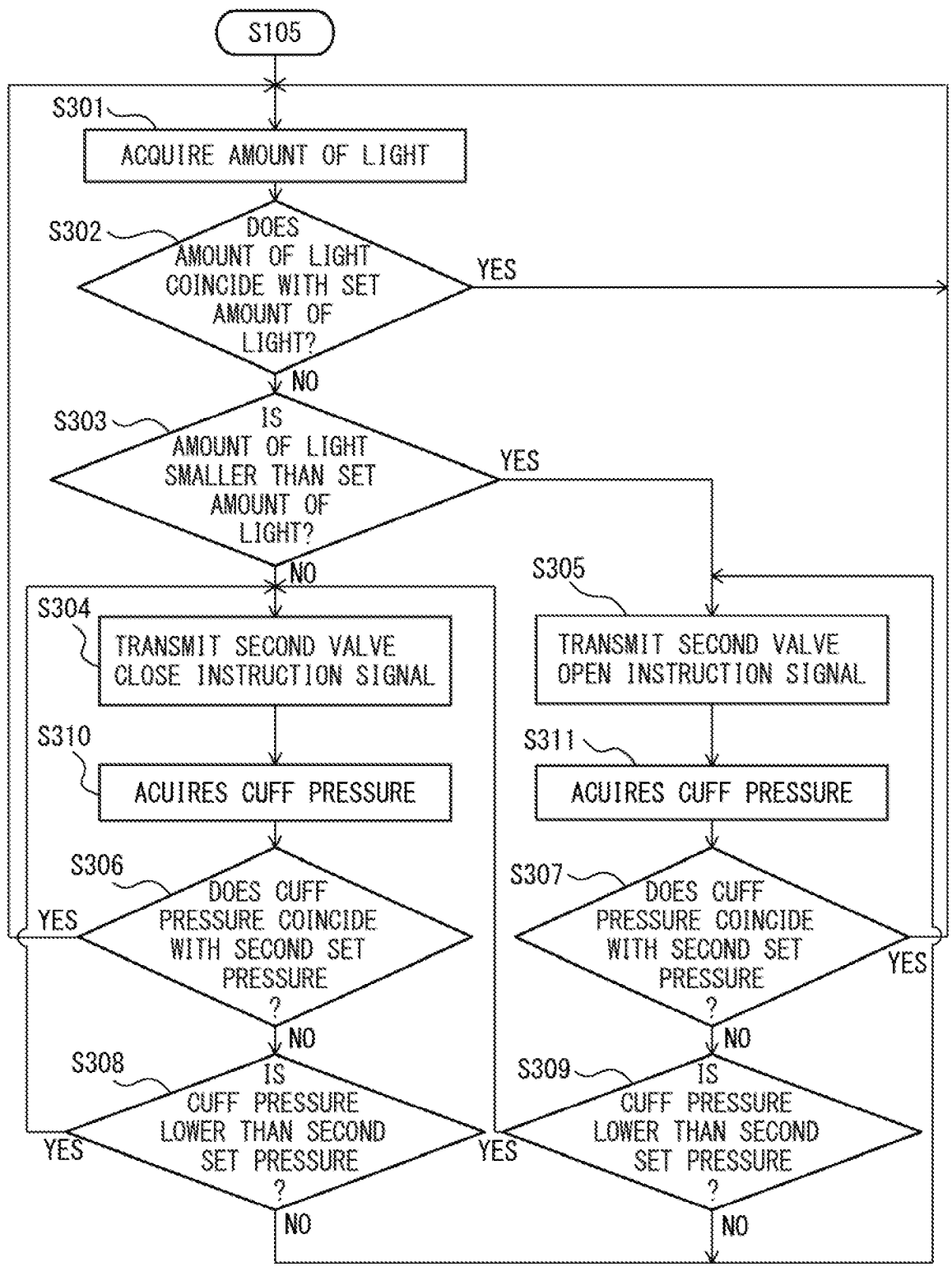
FIG. 10 is a flowchart showing more detailed processing of the processing shown at S105 illustrated in FIG. 8.

FIG. 10 is a flowchart showing more detailed processing of the processing shown at S105.

First, the light amount acquisition unit 53 acquires the amount of light corresponding to the light amount signal transmitted from the light amount detection sensor 18 via the third AD converter 313 (S301).

Next, the second valve opening adjustment unit 56 determines whether the amount of light acquired at S301 coincides with the set amount of light 323 stored in the storage unit 32 (S302). When the second valve opening adjustment unit 56 determines that the amount of light acquired at S301 does not coincide with the set amount of light 323 stored in the storage unit 32 (S302—NO), the second valve opening adjustment unit 56 determines whether the amount of light acquired at S301 is smaller than the set amount of light 323 stored in the storage unit 32 (S303).

When the second valve opening adjustment unit 56 determines that the acquired amount of light is smaller than the set amount of light 323 stored in the storage unit 32 (S303—YES), the second valve opening adjustment unit 56 transmits the second valve open instruction signal to the second valve 23 via the third transmission circuit 316. (S305). When the second valve 23 receives the second valve open instruction signal, the second valve 23 increases the opening by a predetermined change opening. Next, the cuff pressure acquisition unit 55 acquires the cuff pressure inside the cuff 12 corresponding to the cuff pressure signal transmitted from the second pressure sensor 24 via the second AD converter 312 (S311) and determines whether the acquired cuff pressure coincides with that corresponding to the predetermined opening (second set pressure 322) (S307). When they coincide with each other, the processing returns to S301. When it is determined that they do not coincide with each other (S307—NO), whether the acquired cuff pressure is lower than the second set pressure 322 is determined and when the acquired cuff pressure is lower than the second set pressure 322 (S309—YES), the processing returns to S304. When the acquired cuff pressure is higher than the second set pressure 322 (S309—NO), the processing returns to S305.

On the other hand, when the second valve opening adjustment unit 56 determines that the acquired amount of light is larger than the set amount of light 323 stored in the storage unit 32 (S303—NO), the second valve opening adjustment unit 56 transmits the second valve close instruction signal to the second valve 23 via the third transmission circuit 316 (S304). When the second valve 23 receives the second valve close instruction signal, the second valve 23 reduces the opening by a predetermined change opening. Next, the cuff pressure acquisition unit 55 acquires the cuff pressure inside the cuff 12 corresponding to the cuff pressure signal transmitted from the second pressure sensor 24 via the second AD converter 312 (S310) and determines whether the acquired cuff pressure coincides with that corresponding to the predetermined opening (second set pressure) (S306). When they coincide with each other, the processing returns to S301. When it is determined that they do not coincide with each other (S306—NO), whether the acquired cuff pressure is lower than the second set pressure 322 is determined and when the acquired cuff pressure is lower than the second set pressure 322 (S308—YES), the processing returns to S304. When the acquired cuff pressure is higher than the second set pressure 322 (S308—NO), the processing returns to S305.

When it is determined that the acquired amount of light coincides with the set amount of light 323 stored in the storage unit 32 (S302—YES), the processing returns to S301.

Figure 11:
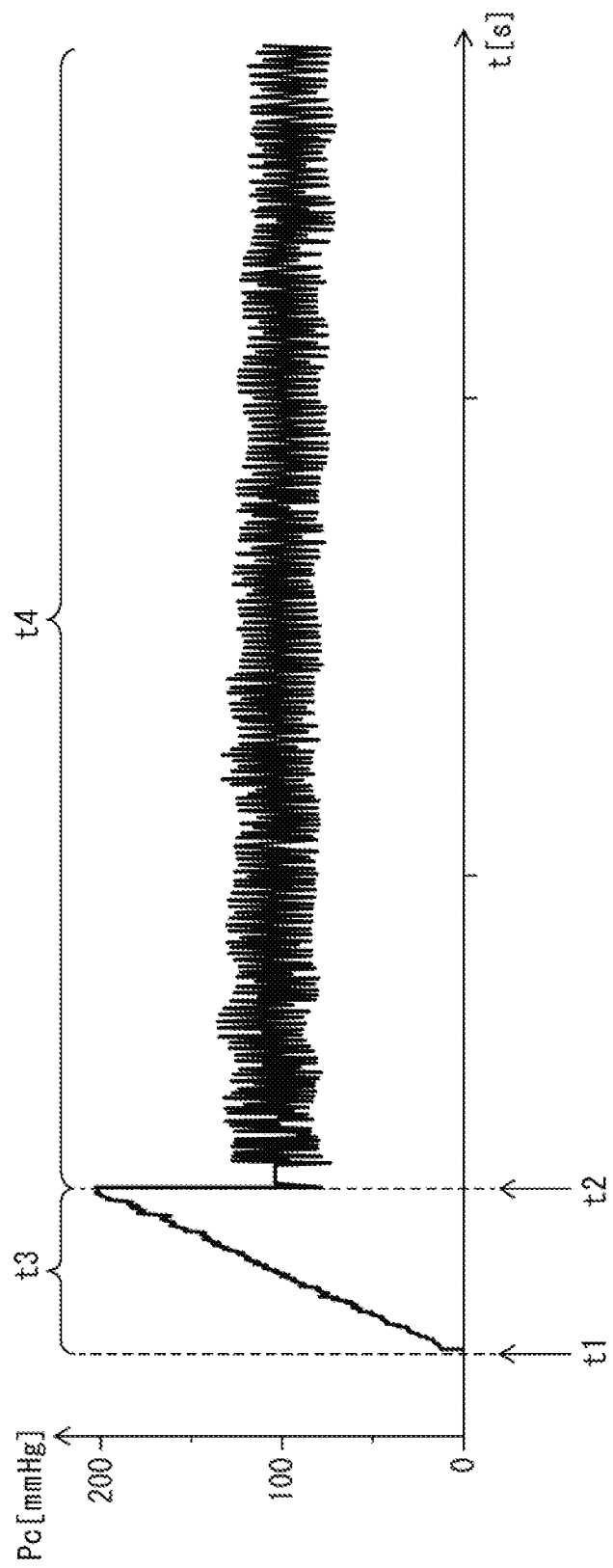
FIG. 11 is a diagram showing an example of the operation of the blood pressure meter illustrated in FIG. 4.

FIG. 11 is a diagram showing an example of the operation of the blood pressure meter 1. In FIG. 11, the horizontal axis represents an elapsed time t [s] and the vertical axis represents a cuff pressure Pc [mmHg] inside the cuff 12.

First, at time t1, the blood pressure measurement instruction determination unit 41 determines that instructions to start blood pressure measurement are acquired from a subject (S101) and instructs the pump 11 to start (S102). When the pump 11 receives the start instruction signal, the pump 11 starts. When the pump 11 starts, the cuff pressure Pc of the vertical axis inside the cuff 12 rises rapidly.

Next, at time t2, the valve opening adjustment unit 42 acquires the discharge pressure of the pump 11 and adjusts the opening of the first valve 13 so that the acquired discharge pressure coincides with the first set pressure (S104). Period of time t3 between time t1 and time t2 is a period of time of preparation until the blood pressure meter 1 starts blood pressure measurement processing.

Period of time t4 after t2 is a period of time of blood pressure measurement during which the blood pressure meter 1 continuously measures the blood pressure of a subject. During period of time t4, by the processing at S103 to S106 being repeated, the cuff pressure Pc varies in accordance with the pulse of a subject.

(Working and Effect of Blood Pressure Meter According to Embodiment)

The blood pressure meter 1 achieves the output of a constant flow rate by maintaining the discharge pressure of the pump 11 in the vicinity of the first set pressure. By adjusting the amount of discharge of the pump 11 by the first valve 13, the variation in the amount of discharge of the pump 11 accompanying the ripple included in the pump is reduced, and therefore the second valve 23 may devote itself to cuff pressure control. Thus, in the blood pressure meter 1, high-speed control of cuff pressure may be implemented that is required when continuously measuring the blood pressure of a subject also by using a general-purpose electromagnetic valve.

Figure 12:
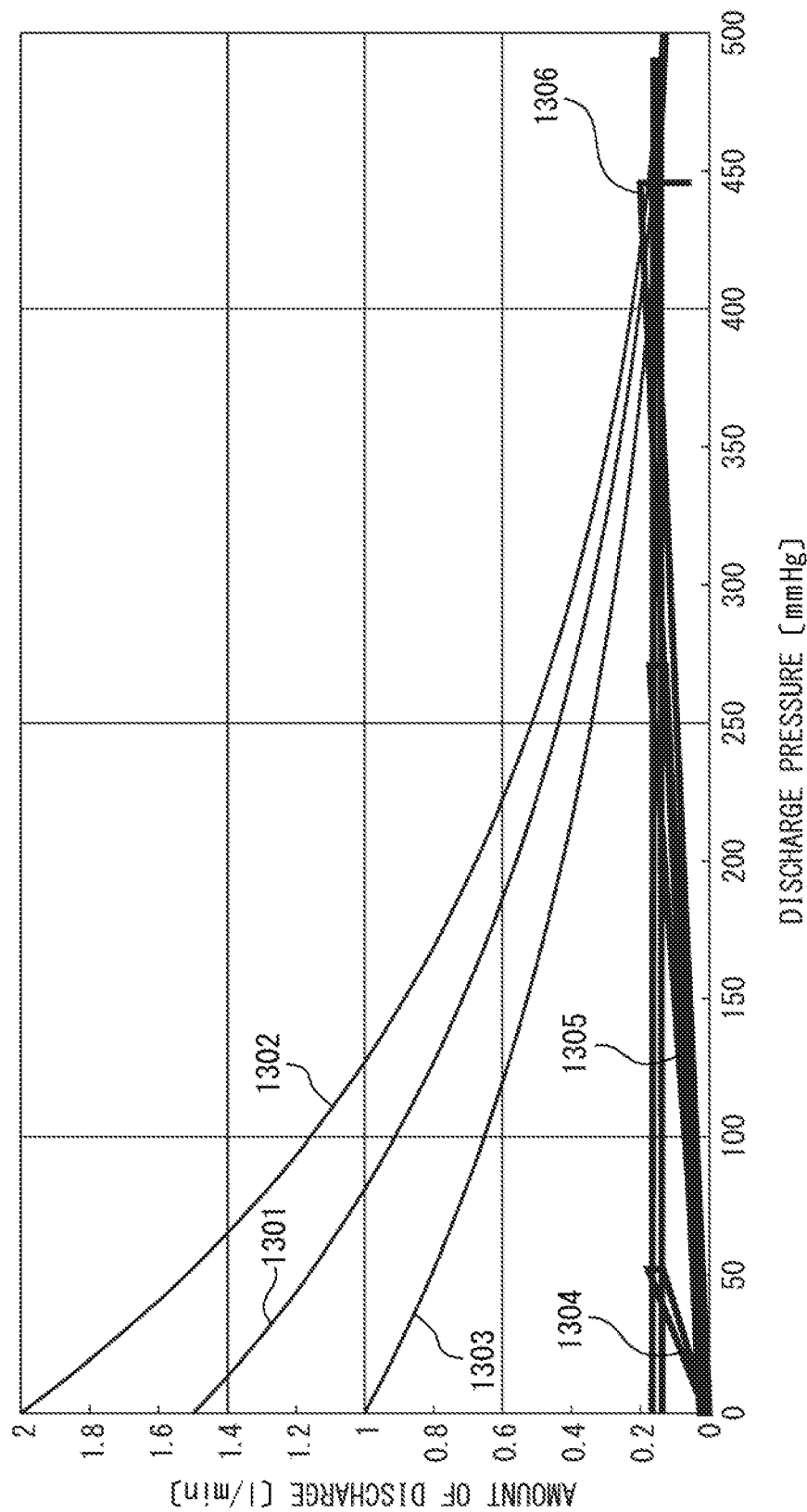
FIG. 12 is a diagram showing pressure/discharge amount characteristics of the pump.

FIG. 12 is a diagram showing pressure/discharge amount characteristics of the pump 11. In FIG. 12, the horizontal axis represents the discharge pressure [mmHg] and the vertical axis represents the amount of discharge [l/min]. Further, a curved line 1301 indicates the curved line 301 shown in FIG. 3, a curved line 1302 indicates the curved line 302 shown in FIG. 3, and a curved line 1303 indicates the curved line 303 shown in FIG. 3. The curved lines 1301 to 1303 indicate the pressure/discharge amount characteristics of the pump 901 of the blood pressure meter 900 explained with reference to FIG. 1 to FIG. 3.

In the blood pressure meter 1, the discharge pressure of the pump 11 is adjusted to 450 [mmHg] by the first valve 13, and therefore the amount of discharge of the pump 11 becomes constant at about 0.18 [ml] as shown in FIG. 12. The load straight line of the first valve 13 used here is included within a range 1306 and the angle formed by two load straight lines is narrow, and therefore an electromagnetic valve whose speed is comparatively slow may be used. In the blood pressure meter 1, the cuff pressure that is changed by following the change in arterial pressure of a person needs only to have follow-up properties of about 20 [Hz]. The range of the load straight line of the second valve 23 when the cuff pressure is varied in a range between 50 [mmHG] is wide, and for the follow-up properties in this range, a speed of about 2.0 Hz described previously is required. On the other hand, in order to remove the influence of the ripple of the pump 11, the range of the load straight line of the second valve 23 becomes a load straight line range 1304 at a cuff pressure of 50 [mmHg] and becomes a load straight line range 1305 at a cuff pressure of 250 [mmHg], and for each range, the angle formed by the two load straight lines is narrow and a valve whose response speed is comparatively slow as the second valve 23 may be used, and therefore cost may be reduced.

Further, in the blood pressure meter 1, the cuff 12 and the first valve 13 are connected via the first cuff connection member 16 in which the first valve 13, the second cuff connection member 17, the second valve 23, and the second pressure sensor 24 are inserted into the four through-holes, and therefore, the volume to which the cuff pressures is applied may be small. In the blood pressure meter 1, the volume to which the cuff pressure is applied is small, and therefore a large change in cuff pressure may be implemented by a small change in the amount of discharge of the pump 11.

All examples and conditional language provided herein are intended for pedagogical purposes of aiding the reader in understanding the invention and the concepts contributed by the inventor to furthering the art, and are to be construed as limitations to such specifically recited examples and conditions, nor does the organization of such examples in the specification relate to a illustrating of the superiority and inferiority of the invention. Although one or more embodiments of the present invention have been described in detail, it should be understood that the various changes, substitutions, and alterations could be made hereto without departing from the spirit and scope of the invention.

REFERENCE SIGNS LIST 1 blood pressure meter
11 pump
12 cuff
13 first valve
14 first pressure sensor
15 pump connection member
16 first cuff connection member
17 second cuff connection member
18 light amount detection sensor (arterial volume information detection sensor)
23 second valve
24 second pressure sensor
30 control device
31 interface unit
32 storage unit
40 processing unit
41 blood pressure measurement instruction determination unit
42 valve opening adjustment unit
43 blood pressure measurement unit

What is claimed is:

1. A blood pressure meter comprising:
a pump;
a cuff configured to be attached to a blood pressure measurement region of a subject;
a first valve arranged between the pump and the cuff and capable of adjusting an amount of discharge of the pump by adjusting an opening;
a second valve capable of adjusting cuff pressure inside the cuff by adjusting an opening;
a first pressure sensor that detects discharge pressure of the pump;
a second pressure sensor that detects the cuff pressure;
an arterial volume information detection sensor that is a photoelectric sensor and detects arterial volume information relating to arterial volume at the blood pressure measurement region of a subject;
a processor configured to perform a process including:
adjusting openings of the first valve and the second valve by acquiring the discharge pressure, the cuff pressure, and the arterial volume information; and
measuring blood pressure of a subject based on the cuff pressure:
a first cuff connection member inside which a first through-hole, a second through-hole, a third through-hole, and a fourth through-hole, each penetrating from an external wall up to a pressure chamber are formed as well as the pressure chamber being formed; and
a second cuff connection member that connects the first cuff connection member and the cuff, wherein
into the first through-hole, the first valve is inserted,
into the second through-hole, the second cuff connection member is inserted,
into the third through-hole, the second valve is inserted, and
into the fourth through-hole, the second pressure sensor is inserted.

2. The blood pressure meter according to claim 1, wherein the adjusting openings includes adjusting an opening of the first valve so that the discharge pressure coincides with a first set pressure.

3. The blood pressure meter according to claim 2, wherein the adjusting openings further includes:
determining a second set pressure so that arterial volume at the blood pressure measurement region becomes constant; and
adjusting an opening of the second valve so that the cuff pressure coincides with the second set pressure.

* * * * *